(12) United States Patent
Moore et al.

(10) Patent No.: US 10,994,059 B2
(45) Date of Patent: May 4, 2021

(54) ANTI-FOULING AND/OR ANTI-THROMBOTIC MEDICAL DEVICES

(71) Applicant: TEKCYTE PTY LTD, Adelaide (AU)

(72) Inventors: Eli Moore, Aberfoyle Park (AU); Nicolas Hans Voelcker, Blackwood (AU); Claudine Sharon Bonder, Prospect (AU)

(73) Assignee: TEKCYTE PTY LTD, Adelaide (AU)

( * ) Notice: Subject to any disclaimer, the term of this patent is extended or adjusted under 35 U.S.C. 154(b) by 0 days.

(21) Appl. No.: 16/085,969

(22) PCT Filed: Mar. 17, 2017

(86) PCT No.: PCT/AU2017/050242
§ 371 (c)(1),
(2) Date: Sep. 17, 2018

(87) PCT Pub. No.: WO2017/156592
PCT Pub. Date: Sep. 21, 2017

(65) Prior Publication Data
US 2019/0076585 A1    Mar. 14, 2019

(30) Foreign Application Priority Data
Mar. 17, 2016   (AU) ................................ 2016901008

(51) Int. Cl.
*A61L 33/06* (2006.01)
*A61L 27/34* (2006.01)
(Continued)

(52) U.S. Cl.
CPC ............ *A61L 33/068* (2013.01); *A61L 27/34* (2013.01); *A61L 29/085* (2013.01); *A61L 31/10* (2013.01); *A61L 33/06* (2013.01); *C08G 65/22* (2013.01)

(58) Field of Classification Search
None
See application file for complete search history.

(56) References Cited

U.S. PATENT DOCUMENTS

2007/0281117 A1* 12/2007 Kaplan .................. A61L 31/10
                                                    428/35.7
2011/0111367 A1    5/2011 Han et al.

FOREIGN PATENT DOCUMENTS

JP    2009-061021 A    3/2009
RU    2542919 C1       2/2015
(Continued)

OTHER PUBLICATIONS

Weber et al., Direct grafting of anti-fouling polyglycerol layers to steel and other technically relevant materials, Colloids and Surfaces B: Biointerfaces, 111(2013)pp. 360-366. (Year: 2013).*

(Continued)

*Primary Examiner* — Carlos A Azpuru
*Assistant Examiner* — Casey S Hagopian
(74) *Attorney, Agent, or Firm* — Fenwick & West LLP

(57) ABSTRACT

The present disclosure relates to anti-fouling and/or anti-thrombotic medical devices, methods for reducing fouling and/or thrombosis associated with medical devices, and methods for coating substrates to reduce fouling and/or thrombosis. Certain embodiments of the present disclosure provide an anti-fouling and/or anti-thrombotic medical device comprising a metallic substrate comprising a hyperbranched polyglycerol coating.

6 Claims, 8 Drawing Sheets

(51) Int. Cl.
    A61L 31/10       (2006.01)
    C08G 65/22       (2006.01)
    A61L 29/08       (2006.01)

(56) References Cited

FOREIGN PATENT DOCUMENTS

WO      WO-0016624 A1 *    3/2000    ............ A61L 29/16
WO      WO 2008/074154 A1  6/2008
WO      WO-2013/037008 A1  3/2013

OTHER PUBLICATIONS

PCT International Search Report & Written Opinion, International Application No. PCT/AU2017/050242, dated Apr. 10, 2017, 8 Pages.

Harrick Plasma, Basic Plasma Cleaner PDC-32G, published Jul. 9, 2014 [Retrieved from the Internet on Sep. 13, 2018] <URL:http://harrickplasma.com/products/basic-plasma-cleaner>.

Weber, T., et al., "Direct grafting of antifouling polyglycerol layers to steel and other technically relevant materials," Colloids and Surfaces B: Biointerfaces, 2013, pp. 360-366, vol. 111.

Khan, M. et al., "Hyperbranched Polyglycidol on Si/SiO2 Surfaces via Surface-Initiated Polymerization" Macromolecules, 2003, vol. 36, pp. 5088-5093.

Moore, E. et al., "Surface-Initiated Hyperbranched Polyglycerol as an Ultralow-Fouling Coating on Glass, Silicon, and Porous Silicon Substrates," ASC Applied Materials & Interfaces, 2014, vol. 6, No. pp. 15243-15252.

Weber, T. et al., "Bacteria-Repulsive Polyglycerol Surfaces by Grafting Polymerization onto Aminopropylated Surfaces" Langmuir, 2012, vol. 28, pp. 15916-15921.

Weber, T. et al., "Direct grafting of anti-fouling polyglycerol layers to steel and other technically relevant materials," Colloids and Surfaces B: Biointerfaces, SciVerse Science Direct, 2013, vol. 111, 7 pages.

European Patent Office, Extended European Search Report and Opinion, EP Patent Application No. 17765584.2, dated Oct. 25, 2019, nine pages.

European Patent Office, Office Action, EP Patent Application No. 17765584.2, dated Oct. 7, 2020, seven pages.

Wei, Q. et al., "Multivalent Anchoring and Cross-Linking of Mussel-Inspired Antifouling Surface Coatings," Biomacromolecules, vol. 15, Aug. 11, 2014, pp. 3061-3071.

* cited by examiner

ANTI-FOULING AND/OR ANTI-THROMBOTIC MEDICAL DEVICES

PRIORITY CLAIM

This application claims priority to Australian provisional patent application number 2016901008 filed on 17 Mar. 2016, the content of which is hereby incorporated by reference.

FIELD

The present disclosure relates to anti-fouling and/or anti-thrombotic medical devices, to methods for reducing fouling and/or and thrombosis associated with medical devices, and to methods for coating substrates to reduce fouling and/or thrombosis.

BACKGROUND

An important consideration in the use of some medical devices is how the device is affected when it is used in vivo, and in particular, how the device is affected when it comes into contact with tissue and fluids. Such considerations are not only important to the performance and/or longevity of the device, but also for reasons of how the use of the medical device may impact upon a patient with the device.

For example, stents are a commonly used medical device to treat a number of conditions. Coronary stents are used during angioplasty to improve blood flow to narrowed or blocked coronary arteries. Stents are also used for peripheral artery angioplasty to treat atherosclerotic narrowing of the abdomen, leg and renal arteries caused by peripheral artery disease, and to assist in the treatment of aneurysms. Typically stents are made from flexible materials, such as flexible metal alloys.

However, while stents are extremely effective as modes of treatment, they suffer a number of disadvantages and/or risks. For example, the use of metal/metal alloy stents carries a risk of stent thrombosis. In the case of the use of coronary stents, stent thrombosis has a major clinical impact owing to a high risk of myocardial infarction and death occurring.

Because metal/metal alloy stents induce platelet adhesion and activation, which can lead to thrombus formation, anti-platelet therapy is usually prescribed after stent implantation, and in some cases such therapy is maintained for the duration of the life of the stent.

In addition, the ability of stents and other medical devices to resist fouling, protein accumulation and/or to reduce platelet attachment and/or activation may have important effects on their usable lifespan, and in the case of stents, their ability to also resist restenosis.

Other types of medical devices, such as cannulas and catheters, can also suffer from the effects of fouling and/or thrombosis, which impacts on their efficacy, longevity and risk of use.

Accordingly, there is a continuing need to provide medical devices with improved properties, and in particular, to provide devices which have reduced thrombotic properties and/or resist fouling.

SUMMARY

The present disclosure relates to anti-fouling and/or anti-thrombotic medical devices, to methods for reducing fouling and/or and thrombosis products associated with medical devices, and to methods for coating substrates to reduce fouling and/or thrombosis.

Certain embodiments of the present disclosure provide an anti-fouling and/or anti-thrombotic medical device, the device comprising a metallic substrate comprising a hyperbranched polyglycerol coating.

Certain embodiments of the present disclosure provide an anti-fouling and/or anti-thrombotic stent, the stent comprising a metallic substrate comprising a hyperbranched polyglycerol coating.

Certain embodiments of the present disclosure provide a method of reducing fouling and/or thrombosis associated with a medical device comprising a metallic substrate, the method comprising coating the metallic substrate with a hyperbranched polyglycerol.

Certain embodiments of the present disclosure provide a method of producing an anti-fouling and/or anti-thrombotic medical device, the method comprising using a hyperbranched polyglycerol coated metallic substrate in the device to reduce fouling and/or thrombosis associated with the medical device.

Certain embodiments of the present disclosure provide a method of coating a metallic substrate with a hyperbranched polyglycerol, the method comprising polymerisation of glycidol monomers to form a hyperbranched polyglycerol on the metallic substrate and thereby coating the substrate with the hyperbranched polyglycerol.

Certain embodiments of the present disclosure provide a method of forming a hyperbranched polyglycerol coating on a metallic substrate, the method comprising exposing the metallic substrate to polymerisation of glycidol monomers and thereby forming a hyperbranched polyglycerol coating on the metallic substrate.

Other embodiments are described herein.

BRIEF DESCRIPTION OF THE FIGURES

Certain embodiments are illustrated by the following figures. It is to be understood that the following description is for the purpose of describing particular embodiments only and is not intended to be limiting with respect to the description.

DETAILED DESCRIPTION

Figure 1:
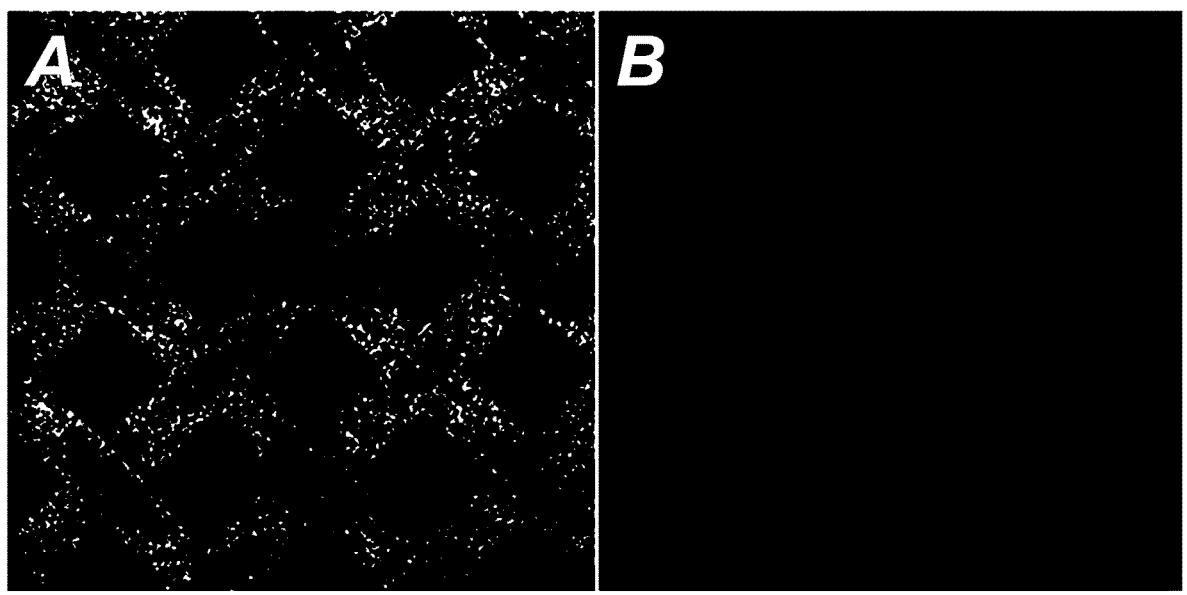
FIG. 1 shows the results using bare 316 stainless steel (SS) mesh with wire diameter of 90 μm (Panel A) and HPG-grafted SS mesh (Panel B) cultured in platelet rich plasma.

The present disclosure relates to anti-fouling and/or anti-thrombotic medical devices, to methods for reducing fouling and/or and thrombosis products associated with medical devices, and to methods for coating substrates to reduce fouling and/or thrombosis.

Certain embodiments of the present disclosure provide a medical device having reduced fouling and/or reduced thrombotic properties.

Certain embodiments of the present disclosure provide an anti-fouling and/or anti-thrombotic medical device, the device comprising a metallic substrate comprising a hyperbranched polyglycerol coating.

In certain embodiments, the device has reduced fouling properties. In certain embodiments, the device is an anti-fouling device.

The term "anti-fouling" as used herein refers to a medical device that has reduced binding of one or more of platelets, cells and/or other cellular material (such as protein), as compared to an untreated medical device.

In certain embodiments, the coating of the metallic substrate with a hyperbranched polyglycerol reduces platelet binding to the substrate, reduces attachment of platelets to the substrate, and/or reduces activation of platelets by the substrate.

In certain embodiments, the coating of the hyperbranched polyglycerol reduces fouling of the substrate by at least 10%, at least 20%, at least 30%, at least 40%, at least 50%, at least 60%, at least 70%, at least 80% or at least 90%, as compared to a medical device that does not have a hyperbranched polyglycerol coating.

In certain embodiments, the coating of the hyperbranched polyglycerol reduces platelet binding/attachment by at least 10%, at least 20%, at least 30%, at least 40%, at least 50%, at least 60%, at least 70%, at least 80% or at least 90%, as compared to a medical device that does not have a hyperbranched polyglycerol coating.

In certain embodiments, the device has reduced thrombotic properties. In certain embodiments, the device is an anti-thrombotic device.

The term "anti-thrombotic" as used herein refers to a medical device that has reduced ability to cause a clot and/or a reduced rated of clotting, as compared to an untreated medical device. It will be appreciated that the reduced clotting associated with the device is not to be limited to clots that form within the device, but also includes other clots associated with the use of the device.

In certain embodiments, the coating of the hyperbranched polyglycerol reduces clotting and/or thrombosis associated with the medical device by at least 10%, at least 20%, at least 30%, at least 40%, at least 50%, at least 60%, at least 70%, at least 80% or at least 90%, as compared to a medical device that does not have a hyperbranched polyglycerol coating.

In certain embodiments, the medical device in use comprises one or more characteristics selected from reduced thrombosis, reduced fouling, reduced attachment of cells and/or proteins, reduced binding/attachment of platelets, reduced activation of platelets, and reduced fibrin formation, as compared to an medical device that does not have a hyperbranched polyglycerol coating.

In certain embodiments, the medical device comprises a stent, a cannula, a catheter, a guide wire, a valve. Other types of medical devices are contemplated.

In certain embodiments, the medical device is a stent. In certain embodiments, the medical device is a vascular stent, such as a coronary stent.

In certain embodiments, the medical device comprises a medical device for use in a vascular setting. In certain embodiments, the medical device comprises a vascular stent or a vascular cannula.

In certain embodiments, the medical device is a stent and the stent is a self-expanding stent or a balloon-expanding stent. Other types of stents are contemplated.

The term "metallic substrate" as used herein refers to a substrate comprising a metallic material, such as a pure metal, a metal alloy, or a mixture of one or more metals and/or other materials. For example, a metallic substrate may be composed entirely of a metal or a metal alloy, or may be composed in part of a metallic material and one or more other materials.

In certain embodiments, the metallic substrate comprises a substantially pure metal. Examples of metals include titanium, nickel, cobalt, chromium, niobium and tantalum. Other types of metals are contemplated. Methods for producing metals for use in medical devices are known in the art.

In certain embodiments, the metallic substrate comprises a metal alloy. Examples of metal alloys include a steel alloy, a nickel containing alloy, a titanium containing alloy, a cobalt contain alloy, or a chromium containing alloy. In certain embodiments, the metallic substrate comprises a steel alloy, a nickel titanium alloy or a cobalt chromium alloy. Other types of alloys are contemplated. Methods for producing metal alloys for use in medical devices are known in the art.

In certain embodiments, the medical device is a stent comprising a steel alloy, a nitinol alloy or a cobalt chromium alloy. In certain embodiments, the medical device is a stainless steel stent, a nitinol stent, or a cobalt chromium stent.

In certain embodiments, the metallic substrate comprises a substrate other than an aluminium substrate. In certain embodiments, the metallic substrate comprises a substrate other than a steel alloy substrate.

The term "hyperbranched polyglycerol" as used herein refers to a branched aliphatic polyether with hydroxyl end groups. It will be appreciated that the term also includes a branched polyether in which a proportion of the hydroxyl end groups have been derivatised and/or replaced with a suitable group.

In certain embodiments, the metallic substrate comprises one or more other coatings, or a coating comprising a hyperbranched polyglycerol and one or more other materials, such as another polymer.

In certain embodiments, the hyperbranched polyglycerol coating comprises a coating formed by a reaction comprising polymerisation of glycidol monomers on the metallic substrate.

In certain embodiments, the polymerisation of the glycidol monomers comprises a ring opening reaction of the glycidol monomers. Other synthetic methods for producing a hyperbranched polyglycerol are contemplated.

In certain embodiments, the coating is formed by a reaction comprising a single (non-iterative) reaction synthesis of monomers. In certain embodiments, the coating is formed by reactions comprising multiple (iterative) reaction syntheses of monomers.

In certain embodiments, the hyperbranched polyglycerol coating is formed by a reaction that does not comprise exposing the metallic substrate to glycidol monomers in the presence of a solvent. In certain embodiments, the hyperbranched polyglycerol coating is formed by a reaction that comprises exposing the metallic substrate to glycidol monomers substantially in the absence of a solvent. In certain embodiments, the hyperbranched polyglycerol coating is formed by exposing the metallic substrate to substantially undiluted glycidol monomers. In certain embodiments, the hyperbranched polyglycerol coating is formed by exposing the metallic substrate to substantially pure glycidol. In certain embodiments, the hyperbranched polyglycerol coating is formed by exposing the metallic substrate to glycidol substantially free of a solvent. In certain embodiments, the hyperbranched polyglycerol coating is formed by exposing the metallic substrate to a solution comprising at least 90% glycidol, at least 95% glycidol, at least 96% glycidol, at least 97% glycidol, at least 98% glycidol, or at least 99% glycidol. The term "solvent" as used herein refers to a substance that dissolves glycidol, and may or may not be chemically inert.

In certain embodiments, the hyperbranched polyglycerol coating is formed by exposing the metallic substrate to a solution comprising substantially pure glycidol or a solution comprising at least 96% glycidol.

In certain embodiments, the coating is formed on an activated metallic substrate. Methods for activation of metallic substrates are known in the art. In certain embodiments, the coating is formed on the metallic substrate activated by plasma treatment. In certain embodiments, the coating is formed on a plasma activated metallic substrate.

Methods for plasma treatment of substrates to form plasma modified surfaces are known in the art. Examples of plasma treatment include radio frequency induced plasma treatment, corona plasma treatment, glow discharge plasma treatment, plasma immersion ion implantation, low pressure plasma treatment, and atmospheric pressure plasma treatment. Other types of plasma treatment are contemplated.

In certain embodiments, the coating is formed on the metallic substrate activated by plasma treatment in the presence of a gas. Examples of gases comprise one or more of oxygen, argon, nitrous oxide, tetrafluoromethane, and air. Other gases are contemplated.

In certain embodiments, the coating is formed on the metallic substrate activated by plasma treatment in the presence of one or more non-depositing and/or inert gases. Examples of non-depositing and/or inert gases include argon and other noble gases such as helium or neon.

In certain embodiments, the coating is formed on the metallic substrate activated by plasma treatment with a gas that does not chemically modify the substrate.

In certain embodiments, the coating is formed on the metallic substrate activated by plasma treatment in the presence of oxygen.

In certain embodiments, the plasma treatment comprises radio frequency induced plasma treatment.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W.

In certain embodiments, the plasma treatment comprises use of a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the coating comprises a thickness of at least 2 nm, at least 3 nm, at least 4 nm, at least 5 nm, at least 6 nm, at least 7 nm, at least 8 nm, at least 9 nm, at least 10 nm, or at least 20 nm. Methods for determining the thickness of the coating are known in the art, for example the use of ellipsometry to determine coating thickness.

In certain embodiments, the coating comprises a thickness selected from 2 nm to 20 nm, 3 nm to 20 nm, 4 nm to 20 nm, 5 nm to 20 nm, 6 nm to 20 nm, 7 nm to 20 nm, 8 nm to 20 nm, 9 nm to 20 nm, 10 nm to 20 nm, 11 nm to 20 nm, 12 nm to 20 nm, 13 nm to 20 nm, 14 nm to 20 nm, 15 nm to 20 nm, 16 nm to 20 nm, 17 nm to 20 nm, 18 nm to 20 nm, or 19 to 20 nm.

In certain embodiments, the coating comprises a thickness selected from 5 nm to 10 nm, 6 nm to 10 nm, 7 nm to 10 nm, 8 nm to 10 nm, 9 nm to 10 nm, 5 nm to 9 nm, 6 nm to 9 nm, 7 nm to 9 nm, 8 nm to 9 nm, 5 nm to 8 nm, 6 nm to 8 nm, 7 nm to 8 nm, 5 nm to 7 nm, 6 nm to 7 nm, or 5 to 6 nm.

In certain embodiments, the coating is formed directly on the metallic substrate. In certain embodiments, the coating is formed directly on a plasma activated metallic substrate.

In certain embodiments, the metallic substrate is activated by plasma treatment and the coating is formed on the activated metallic substrate.

In certain embodiments, the coating is formed indirectly on the metallic substrate.

In certain embodiments, the coating is formed on a functionalised metallic substrate. In certain embodiments, the metallic substrate is functionalised and the coating is formed on the functionalised metallic substrate. Methods for functionalisation of substrates/surfaces are known in the art. Methods for formation of polymers or other materials on a functionalised substrate/surface are known in the art.

Certain embodiments of the present disclosure provide use of a medical device as described herein, for example to prevent and/or treat a condition selected from arterial or venous narrowing, angina, an aneurysm, or to repair or support an artery or vein. Other conditions or uses of the medical device are contemplated.

As described herein, in certain embodiments the medical device is a stent.

Certain embodiments of the present disclosure provide an anti-fouling and/or an anti-thrombotic stent, the stent comprising a metallic substrate comprising a hyperbranched polyglycerol coating.

Examples of stents are described herein. In certain embodiments, the stent is a coronary stent.

Certain embodiments of the present disclosure provide the use of a stent as described herein, for example to treat a vascular condition.

Certain embodiments of the present disclosure provide a method of treating a vascular condition in a subject that would benefit from the introduction of a stent, the method comprising using a stent as described herein to treat the vascular condition.

In certain embodiments, the vascular condition comprises arterial or venous narrowing, angina, an aneurysm, or repair or support of an artery or vein. Other conditions are contemplated. Methods for using a stent to treat such conditions are known in the art.

Certain embodiments of the present disclosure provide a method of reducing fouling and/or thrombosis associated with a medical device.

Certain embodiments of the present disclosure provide a method of reducing fouling and/or thrombosis associated with a medical device comprising a metallic substrate, the method comprising coating the metallic substrate with a hyperbranched polyglycerol.

In certain embodiments, the reduction of fouling and/or thrombosis comprises one or more of a reduction in attachment of cells and/or proteins to the substrate, a reduction in attachment of platelets to the substrate, a reduction in the activation of platelets by the substrate and a reduction in fibrin formation on the substrate.

In certain embodiments, the method results in a reduction of fouling by at least 10%, at least 20%, at least 30%, at least 40%, at least 50%, at least 60%, at least 70%, at least 80% or at least 90%, as compared to a medical device that does not have a hyperbranched polyglycerol coating.

In certain embodiments, the method results in a reduction of fouling of the metallic substrate by at least 10%, at least 20%, at least 30%, at least 40%, at least 50%, at least 60%, at least 70%, at least 80% or at least 90%, as compared to uncoated metallic substrate.

In certain embodiments, the method results in a reduction of clotting and/or thrombosis associated with the medical device by at least 10%, at least 20%, at least 30%, at least 40%, at least 50%, at least 60%, at least 70%, at least 80% or at least 90%, as compared to a medical device that does not have a hyperbranched polyglycerol coating.

In certain embodiments, the method results in a reduction of clotting and/or thrombosis associated with the metallic substrate by at least 10%, at least 20%, at least 30%, at least 40%, at least 50%, at least 60%, at least 70%, at least 80% or at least 90%, as compared to uncoated metallic substrate.

Medical devices are as described herein. In certain embodiments, the medical device comprises a stent, a cannula, a catheter, a guide wire, a valve. Other types of medical devices are contemplated.

In certain embodiments, the medical device comprises a medical device for use in a vascular setting. In certain embodiments, the medical device comprises a vascular stent or a vascular cannula. In certain embodiments, the medical device is a stent, such as a coronary stent.

Metallic substrates are as described herein. In certain embodiments, the metallic substrate comprises a substantially pure metal. Examples of metals include titanium, nickel, cobalt, chromium, niobium and tantalum. Other types of metals are contemplated. Methods for producing metals for use in medical devices are known in the art.

In certain embodiments, the metallic substrate comprises a metal alloy. Examples of metal alloys include a steel alloy, a nickel containing alloy, a titanium containing alloy, a cobalt contain alloy, or a chromium containing alloy. In certain embodiments, the metallic substrate comprises a steel alloy, a nickel titanium alloy or a cobalt chromium alloy. Other types of alloys are contemplated. Methods for producing metal alloys for use in medical devices are known in the art.

In certain embodiments, the medical device is a steel alloy stent, a nickel titanium alloy stent or a cobalt chromium alloy stent.

In certain embodiments, the metallic substrate comprises a substrate other than an aluminium substrate. In certain embodiments, the metallic substrate comprises a substrate other than a steel alloy substrate.

Examples of coatings, and methods for forming coatings, include those described herein.

In certain embodiments, the method comprises coating the metallic substrate with one or more other coatings, or coating with the hyperbranched polyglycerol and one or more other materials, such as another polymer.

In certain embodiments, the coating of the metallic substrate comprises polymerisation of glycidol monomers on the metallic substrate.

In certain embodiments, the polymerisation of the glycidol monomers comprises a ring opening reaction of the glycidol monomers. Other synthetic methods are contemplated.

In certain embodiments, the coating of the metallic substrate comprises activation of the metallic substrate. In certain embodiments, the coating of the metallic substrate comprises activation of the metallic substrate by plasma treatment.

In certain embodiments, the coating of the metallic substrate comprises activation of the metallic substrate by plasma treatment in the presence of a gas. Examples of gases comprise one of more of oxygen, argon, nitrous oxide, tetrafluoromethane, and air.

In certain embodiments, the coating of the metallic substrate comprises activation of the metallic substrate by plasma treatment in the presence of one or more non-depositing and/or inert gases.

In certain embodiments, the coating of the metallic substrate comprises activation of the metallic substrate by plasma treatment in the presence of oxygen.

In certain embodiments, the plasma treatment comprises radio frequency induced plasma treatment. Other types of plasma treatment are contemplated.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W.

In certain embodiments, the plasma treatment comprises use of a pressure of $1.0\times10^{-3}$ bar or more, $5.0\times10^{-3}$ bar or more, $8.0\times10^{-3}$ bar or more, $1\times10^{-2}$ bar or more, $2.0\times10^{-2}$ bar or more, or $5.0\times10^{-2}$ bar or more.

In certain embodiments, the plasma treatment comprises use of a pressure of $1.0\times10^{-3}$ bar or less, $5.0\times10^{-3}$ bar or less, $8.0\times10^{-3}$ bar or less, $1\times10^{-2}$ bar or less, $2.0\times10^{-2}$ bar or less, or $5.0\times10^{-2}$ bar or less.

In certain embodiments, the coating of the metallic substrate comprises formation of the coating directly on the metallic substrate. In certain embodiments, the coating is formed directly on plasma activated substrates.

In certain embodiments, the metallic substrate is activated by plasma treatment and the coating is formed on the activated substrate.

In certain embodiments, the metallic substrate is activated by plasma treatment in the presence of an inert and/or non-depositing gas, such as argon.

In certain embodiments, the metallic substrate is activated by plasma treatment with a gas that does not chemically modify the substrate.

In certain embodiments, the coating is formed indirectly on the substrate.

In certain embodiments, the coating is formed on a functionalised substrate. In certain embodiments, the substrate is functionalised and the coating is formed on the functionalised substrate. Methods for functionalisation of substrates are known in the art. Methods for formation of polymers or other materials on a functionalised substrate are known in the art.

In certain embodiments, the method does not comprise exposing the metallic substrate to the glycidol monomers in the presence of a solvent. In certain embodiments, the hyperbranched polyglycerol coating is formed by a reaction that comprise exposing the metallic substrate to glycidol monomers substantially in the absence of a solvent. In certain embodiments, the method comprises exposing the metallic substrate to undiluted glycidol monomers. In certain embodiments, the method comprises exposing the metallic substrate to substantially pure glycidol. In certain embodiments, the method comprises exposing the metallic substrate to glycidol substantially free of a solvent. In certain embodiments, the method comprises exposing the metallic substrate to a solution comprising at least 90% glycidol, at least 95% glycidol, at least 96% glycidol, at least 97% glycidol, at least 98% glycidol, or at least 99% glycidol.

In certain embodiments, the method comprises exposing the metallic substrate to a solution comprising substantially pure glycidol or a solution comprising at least 96% glycidol.

In certain embodiments, the method comprises forming a coating having a thickness of at least 2 nm, at least 3 nm, at least 4 nm, at least 5 nm, at least 6 nm, at least 7 nm, at least 8 nm, at least 9 nm, at least 10 nm, or at least 20 nm. Methods for determining the thickness of the coating are known in the art, for example the use of ellipsometry to determine coating thickness.

In certain embodiments, the method comprises forming a coating having a thickness selected from 2 nm to 20 nm, 3 nm to 20 nm, 4 nm to 20 nm, 5 nm to 20 nm, 6 nm to 20 nm, 7 nm to 20 nm, 8 nm to 20 nm, 9 nm to 20 nm, 10 nm to 20 nm, 11 nm to 20 nm, 12 nm to 20 nm, 13 nm to 20 nm, 14 nm to 20 nm, 15 nm to 20 nm, 16 nm to 20 nm, 17 nm to 20 nm, 18 nm to 20 nm, or 19 to 20 nm.

In certain embodiments, the method comprises forming a coating having a thickness selected from 5 nm to 10 nm, 6 nm to 10 nm, 7 nm to 10 nm, 8 nm to 10 nm, 9 nm to 10 nm, 5 nm to 9 nm, 6 nm to 9 nm, 7 nm to 9 nm, 8 nm to 9 nm, 5 nm to 8 nm, 6 nm to 8 nm, 7 nm to 8 nm, 5 nm to 7 nm, 6 nm to 7 nm, or 5 to 6 nm.

Certain embodiments of the present disclosure provide a medical device with reduced fouling and/or thrombosis produced by coating the device using a method as described herein.

Certain embodiments of the present disclosure provide a medical device comprising a metallic substrate coated with a hyperbranched polyglycerol.

Certain embodiments of the present disclosure provide a method of coating a metallic substrate with a hyperbranched polyglycerol.

Certain embodiments of the present disclosure provide a method of coating a metallic substrate with a hyperbranched polyglycerol, the method comprising polymerisation of glycidol monomers to form a hyperbranched polyglycerol on the metallic substrate and thereby coating the metallic substrate with the hyperbranched polyglycerol.

In certain embodiments, the coating of the metallic substrate results in the substrate in use in an in vivo setting, such as a vascular setting, comprising one or more characteristics selected from reduced fouling of the substrate, reduced thrombosis associated with the substrate, reduced attachment of cells and/or proteins to the substrate coated, reduced attachment of platelets to the substrate, reduced activation of platelets by the substrate, and reduced fibrin formation on the substrate, and low level complement activation.

In certain embodiments, the metallic substrate forms part of a medical device. Medical devices are as described herein. Other uses of the coated metallic substrate are contemplated.

In certain embodiments, the coated metallic substrate is used in a medical device for use in a vascular setting. In certain embodiments, the medical device is a stent, such as a coronary stent.

Metallic substrates are described herein.

In certain embodiments, the metallic substrate comprises a substantially pure metal. Examples of metals include titanium, nickel, cobalt, chromium, niobium and tantalum. Other types of metals are contemplated. Methods for producing metals for use in medical devices are known in the art.

In certain embodiments, the metallic substrate comprises a metal alloy. Examples of metal alloys include a steel alloy, a nickel containing alloy, a titanium containing alloy, a cobalt contain alloy, or a chromium containing alloy. In certain embodiments, the metallic substrate comprises a steel alloy, a nickel titanium alloy or a cobalt chromium alloy. Other types of alloys are contemplated. Methods for producing metal alloys for use in medical devices are known in the art.

In certain embodiments, the metallic substrate comprises a substrate other than an aluminium substrate. In certain embodiments, the metallic substrate comprises a substrate other than a steel alloy substrate.

Coatings, and methods for forming coatings on metallic substrates, are as described herein.

In certain embodiments, the method comprises forming one or more other coatings on the metallic substrate, or forming a coating on the metallic substrate with the hyperbranched polyglycerol and one or more other materials, such as another polymer.

In certain embodiments, the polymerisation of the glycidol monomers comprises a ring opening reaction of the glycidol monomers. Other synthetic methods are contemplated.

In certain embodiments, the method comprises activation of the metallic substrate. Methods for activating metallic substrates are known in the art. In certain embodiments, the method comprises activation of the metallic substrate by plasma treatment. Methods for plasma treatment of substrates to form plasma modified surfaces are known in the art.

In certain embodiments, the method comprises activation of the metallic substrate by plasma treatment in the presence of a gas. Examples of gases comprise one of more of oxygen, argon, nitrous oxide, tetrafluoromethane, and air.

In certain embodiments, the method comprises activation of the metallic substrate by plasma treatment in the presence of one or more inert and/or non-depositing gases. Examples of non-depositing and/or inert gases include argon and other noble gases such as helium or neon.

In certain embodiments, the metallic substrate is activated by plasma treatment with a gas that does not chemically modify the substrate.

In certain embodiments, the method comprises activation of the metallic substrate by plasma treatment in the presence of oxygen.

In certain embodiments, the plasma treatment comprises radio frequency induced plasma treatment. Other types of plasma treatment are contemplated.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W.

In certain embodiments, the plasma treatment comprises use of a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the method comprises polymerisation of the glycidol monomers directly on the metallic substrate. In certain embodiments, the method comprises formation of the coating directly on plasma activated metallic substrate.

In certain embodiments, method comprises polymerisation of the glycidol monomers on the metallic substrate activated by plasma treatment.

In certain embodiments, the method comprises polymerisation of the glycidol monomers indirectly on the metallic substrate.

In certain embodiments, the method comprises polymerisation of the glycidol monomers on functionalised metallic substrate.

Methods for functionalisation of substrates are known in the art. Methods for formation of polymers or other materials on a functionalised substrate are known in the art.

In certain embodiments, the method does not comprise exposing the metallic substrate to the glycidol monomers in the presence of a solvent. In certain embodiments, the hyperbranched polyglycerol coating is formed by a reaction that comprise exposing the metallic substrate to glycidol monomers substantially in the absence of a solvent. In certain embodiments, the method comprises exposing the metallic substrate to undiluted glycidol monomers. In certain embodiments, the method comprises exposing the metallic substrate to substantially pure glycidol. In certain embodiments, the method comprises exposing the metallic substrate to glycidol substantially free of a solvent. In certain embodiments, the method comprises exposing the metallic substrate to a solution comprising at least 90% glycidol, at least 95% glycidol, at least 96% glycidol, at least 97% glycidol, at least 98% glycidol, or at least 99% glycidol.

In certain embodiments, the method comprises exposing the metallic substrate to a solution comprising substantially pure glycidol or a solution comprising at least 96% glycidol.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W.

In certain embodiments, the plasma treatment comprises treatment using a power in the range of 10 W or greater. In certain embodiments, the plasma treatment comprises treatment using a power in the range of 100 W to 500 W.

In certain embodiments, the plasma treatment comprises use of a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar. Other pressures are contemplated.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the method comprises forming a coating having a thickness of at least 2 nm, at least 3 nm, at least 4 nm, at least 5 nm, at least 6 nm, at least 7 nm, at least 8 nm, at least 9 nm, at least 10 nm, or at least 20 nm. Methods for determining the thickness of the coating are known in the art, for example the use of ellipsometry to determine coating thickness.

In certain embodiments, the method comprises forming a coating having a thickness selected from 2 nm to 20 nm, 3 nm to 20 nm, 4 nm to 20 nm, 5 nm to 20 nm, 6 nm to 20 nm, 7 nm to 20 nm, 8 nm to 20 nm, 9 nm to 20 nm, 10 nm to 20 nm, 11 nm to 20 nm, 12 nm to 20 nm, 13 nm to 20 nm, 14 nm to 20 nm, 15 nm to 20 nm, 16 nm to 20 nm, 17 nm to 20 nm, 18 nm to 20 nm, or 19 to 20 nm.

In certain embodiments, the method comprises forming a coating having a thickness selected from 5 nm to 10 nm, 6 nm to 10 nm, 7 nm to 10 nm, 8 nm to 10 nm, 9 nm to 10 nm, 5 nm to 9 nm, 6 nm to 9 nm, 7 nm to 9 nm, 8 nm to 9 nm, 5 nm to 8 nm, 6 nm to 8 nm, 7 nm to 8 nm, 5 nm to 7 nm, 6 nm to 7 nm, or 5 to 6 nm.

Certain embodiments of the present disclosure provide a metallic substrate coated by a method as described herein.

Certain embodiments of the present disclosure provide a medical device comprising a coated metallic substrate as described herein.

Certain embodiments of the present disclosure provide a method of forming a hyperbranched polyglycerol coating on a metallic substrate.

Certain embodiments of the present disclosure provide a method of forming a hyperbranched polyglycerol coating on a metallic substrate, the method comprising exposing the metallic substrate to polymerisation of glycidol monomers and thereby form a hyperbranched polyglycerol coating on the metallic substrate.

In certain embodiments, the formation of the coating on the metallic substrate results in the substrate in use in vivo, such as in a vascular setting, comprising one or more characteristics selected from reduced fouling of the substrate, reduced thrombosis associated with the substrate, reduced attachment of cells and/or proteins to the substrate coated, reduced attachment of platelets to the substrate, reduced activation of platelets by the substrate, and reduced fibrin formation on the substrate.

In certain embodiments, the metallic substrate forms part of a medical device. Medical devices are as described herein. In certain embodiments, the medical device comprises a medical device for use in a vascular setting. In certain embodiments, the medical device is a stent, such as a coronary stent.

Metallic substrates are described herein. In certain embodiments, the metallic substrate comprises a substantially pure metal. Examples of metals include titanium, nickel, cobalt, chromium, niobium and tantalum. Other types of metals are contemplated. Methods for producing metals for use in medical devices are known in the art.

In certain embodiments, the metallic substrate comprises a steel alloy, a nickel containing alloy, a titanium containing alloy, a cobalt contain alloy, or a chromium containing alloy. In certain embodiments, the metallic substrate comprises a steel alloy, a nickel titanium alloy (eg nitinol) or a cobalt chromium alloy. Other types of metallic substrates are contemplated.

In certain embodiments, the metallic substrate comprises a substrate other than an aluminium substrate. In certain embodiments, the metallic substrate comprises a substrate other than a steel alloy substrate.

Examples of coatings, and methods for forming coatings, are included herein.

In certain embodiments, the method comprises forming one or more other coatings on the metallic substrate and/or forming a coating on the metallic substrate with the hyperbranched polyglycerol and one or more other materials, such as another polymer.

In certain embodiments, the polymerisation of the glycidol monomers comprises a ring opening reaction of the glycidol monomers. Other synthetic methods are contemplated.

In certain embodiments, the method comprises activation of the metallic substrate. In certain embodiments, the method comprises activation of the metallic substrate by plasma treatment. Methods for plasma treatment of substrates to form plasma modified surfaces are known in the art.

In certain embodiments, the method comprises activation of the metallic substrate by plasma treatment in the presence of a gas. Examples of gases comprise one of more of oxygen, argon, nitrous oxide, tetrafluoromethane, and air.

In certain embodiments, the method comprises activation of the metallic substrate by plasma treatment in the present of an inert and/or non-depositing gas, such as argon.

In certain embodiments, the method comprises activation of the metallic substrate by plasma treatment with a gas that does not chemically modify the substrate. For example, plasma polymerisation in the presence of an inert gas such as argon modifies the substrate by producing charged and free radical species which can initiate polymerisation, while plasma polymerisation in the presence of oxygen produces charged oxygen species in the substrate that can initiate polymerisation.

In certain embodiments, the method comprises activation of the metallic substrate by plasma treatment in the presence of oxygen.

In certain embodiments, the plasma treatment comprises radio frequency induced plasma treatment. Other types of plasma treatment are contemplated.

In certain embodiments, the plasma treatment comprises treatment using a power in the range of 10 W or greater, 20 W or greater, 50 W or greater or 100 W or greater. In certain embodiments, the plasma treatment comprises treatment using a power in the range of 10 W or greater.

In certain embodiments, the plasma treatment comprises treatment using a power in the range of 10 W to 500 W, 10 to 100 W, 20 to 500 W, 20 to 100 W, 50 to 500 W, 50 to 100 W, or 100 to 500 W. In certain embodiments, the plasma treatment comprises treatment using a power in the range of 100 W to 500 W.

In certain embodiments, the plasma treatment comprises use of a pressure of $1.0 \times 10^{-3}$ bar or more, $5.0 \times 10^{-3}$ bar or more, $8.0 \times 10^{-3}$ bar or more, $1 \times 10^{-2}$ bar or more, $2.0 \times 10^{-2}$ bar or more, or $5.0 \times 10^{-2}$ bar.

In certain embodiments, the plasma treatment comprises use of a pressure of $1.0 \times 10^{-3}$ bar or less, $5.0 \times 10^{-3}$ bar or less, $8.0 \times 10^{-3}$ bar or less, $1 \times 10^{-2}$ bar or less, $2.0 \times 10^{-2}$ bar or less, or $5.0 \times 10^{-2}$ bar or less.

In certain embodiments, the method comprises polymerisation of the glycidol monomers directly on the metallic substrate. In certain embodiments, the method comprises formation of the coating directly on the plasma activated metallic substrate.

In certain embodiments, method comprises polymerisation of the glycidol monomers on the metallic substrate activated by plasma treatment.

In certain embodiments, the method comprises polymerisation of the glycidol monomers indirectly on the metallic substrate.

In certain embodiments, the method comprises polymerisation of the glycidol monomers on functionalised metallic substrate.

Methods for functionalisation of substrates are known in the art. Methods for formation of polymers or other materials on a functionalised substrate are known in the art.

In certain embodiments, the method does not comprise exposing the metallic substrate to the glycidol monomers in the presence of a solvent. In certain embodiments, the hyperbranched polyglycerol coating is formed by a reaction that comprises exposing the metallic substrate to glycidol monomers substantially in the absence of a solvent. In certain embodiments, the method comprises exposing the metallic substrate to undiluted glycidol monomers. In certain embodiments, the method comprises exposing the metallic substrate to substantially pure glycidol. In certain embodiments, the method comprises exposing the metallic substrate to glycidol substantially free of a solvent. In certain embodiments, the method comprises exposing the metallic substrate to a solution comprising at least 90% glycidol, at least 95% glycidol, at least 96% glycidol, at least 97% glycidol, at least 98% glycidol, or at least 99% glycidol.

In certain embodiments, the method comprises exposing the exposing the metallic substrate to a solution comprising substantially pure glycidol or a solution comprising at least 96% glycidol.

Certain embodiments of the present disclosure provide a hyperbranched polyglycerol coated metallic substrate produced by a method as described herein.

Certain embodiments of the present disclosure provide a method of producing an anti-fouling and/or anti-thrombotic medical device/

Certain embodiments of the present disclosure provide a method of producing an anti-fouling and/or anti-thrombotic medical device, the method comprising using a hyperbranched polyglycerol coated metallic substrate in the device to reduce fouling and/or thrombosis associated with the medical device.

Certain embodiments of the present disclosure provide a method of producing an anti-fouling and/or anti-thrombotic medical device, the method comprising coating a medical device comprising a metallic substrate with a hyperbranched polyglycerol.

Methods for assessing fouling are known in the art, and include for example, visualisation of the material for attached matter (eg proteins, cells, platelets) by light microscopy.

Methods for assessing clotting or thrombosis are known in the art, and include for example, assessment of implanted materials for the presence of a clot/thrombus and/or in vitro studies as described herein.

The present disclosure is further described by the following examples. It is to be understood that the following description is for the purpose of describing particular embodiments only and is not intended to be limiting with respect to the above description.

Example 1—Grafting of Hyperbranched Polyglycerol onto Metallic Substrates Methodology Glycidol (Sigma, 96%) was distilled at 60° C. under vacuum and stored in sealed 1.5 mL eppendorf tubes at −20° C. until required.

Metallic substrates (Stainless steel 316, Nitinol and Cobalt-Chromium alloys) were sonicated in dichloromethane (DCM) for 10 minutes and then a further 5 minutes in fresh DCM to remove organic contaminants.

The clean substrates were dried under a stream of nitrogen gas and placed at the centre of the vacuum chamber of a plasma cleaner fitted with an oxygen gas line-in. Substrates were either placed directly on a quartz crystal shelf or suspended from a stainless steel wire frame purpose built for positioning stents at the centre of the chamber. The vacuum chamber was pumped down to a pressure ≤$2.0 \times 10^{-2}$ mbar with intermittent purging with pure oxygen to ensure minimal atmospheric contamination in the chamber.

Upon reaching the desired pressure, radio frequency (RF) induced plasma was ignited at maximum power (18 W RF output) for 20 minutes.

Following plasma treatment the chamber was backfilled with pure oxygen and the samples transferred directly into distilled glycidol. The samples were then incubated at 100° C. for up to 24 hours.

Following incubation the unreacted glycidol was removed and samples washed ×3 with 100% ethanol and then soaked in 100% ethanol for at least 24 hours.

The process described above resulted in coating of stainless steel 316, Nitinol and Cobalt-Chromium alloys with a hyperbranched polyglycerol. The substrates were activated through a radio frequency (RF) induced plasma process free of organic solvents. Immediate immersion of the activated substrates in neat (solvent free) glycidol initiated ring-opening polymerisation of the monomer directly from the surface.

XPS data obtained indicated that the coating formed had a thickness of less than 10 nm.

The process of grafting hyperbranched polyglycerol (HPG) onto the substrate using undiluted glycidol has also been found to provide additional improvements in the rate of coating of the substrate. For example, the method as described herein using undiluted glycidol results in growth of the coating on stainless steel to greater than 10 nm in 3 hours at 100° C. This data demonstrates that diluting of glycidol is detrimental to the coating process. Improvements in the rate of growth of the coating provide, amongst other benefits, benefits in commercial production.

The process of grafting hyperbranched polyglycerol (HPG) from any metallic substrate provides a green chemistry process that can be readily implemented on an industrial scale and inserted into existing production lines for processing relevant medical devices. The use of undiluted glycidol also removes the need to remove any organic solvent waste, and any unreacted glycidol can be reused (for example re-purified by re-distillation) resulting in reduced wastage of the monomer.

Example 2—Grafting of Hyperbranched Polyglycerol onto Metallic Substrates Results in Anti-Fouling and Anti-Thrombotic Properties Methodology Platelet rich plasma (PRP) was isolated from human whole blood donated by a healthy non-smoker adult. Whole blood was collected into BD Vacutainer containing 1 mL of ACD (Acid citrate dextrose) solution B then transferred into plastic centrifuge tubes. The whole blood was spun at 250 g for 15 minutes with no brake. PRP was taken from the top portion of the supernatant (platelet count=193 million cells/mL, white blood cells=1.32 million cells/mL).

HPG-grafted stainless steel, nitinol and cobalt chromium stents, along with the controls, were washed ×3 with sterile PBS (pH 7.4) then incubated in freshly isolated PRP for 2 hours at 37° C. and 5% $CO_2$.

Following incubation, stents were washed lightly ×3 with warm PBS and fixed with paraformaldehyde solution (4% in PBS) for 20 minutes. Fixed stents were washed ×3 with PBS and stained with CFSE (Carboxyfluorescein succinimidyl ester) and DAPI (4',6-diamidino-2-phenylindole) (1:2000 in PBS pH 7.4) for 20 minutes at 37° C., then washed ×3 with PBS and ×3 with deionised water.

Substrates were imaged on a Zeiss 710 confocal microscope.

Results

The effect of HPG coating on a bare stainless steel mesh was initially investigated.

FIG. 1 shows the results using a bare 316 stainless steel (SS) mesh with wire diameter of 90 μm (Panel A) and HPG-grafted SS mesh (Panel B).

Platelets could clearly be observed to attach in high numbers to the bare SS while the HPG-grafted SS remained almost completely platelet free. These studies indicated that the HPG modified stainless steel mesh had a greatly reduced platelet attachment.

The effect of HPG on a Nitinol expanding stent was next investigated.

Figure 2:
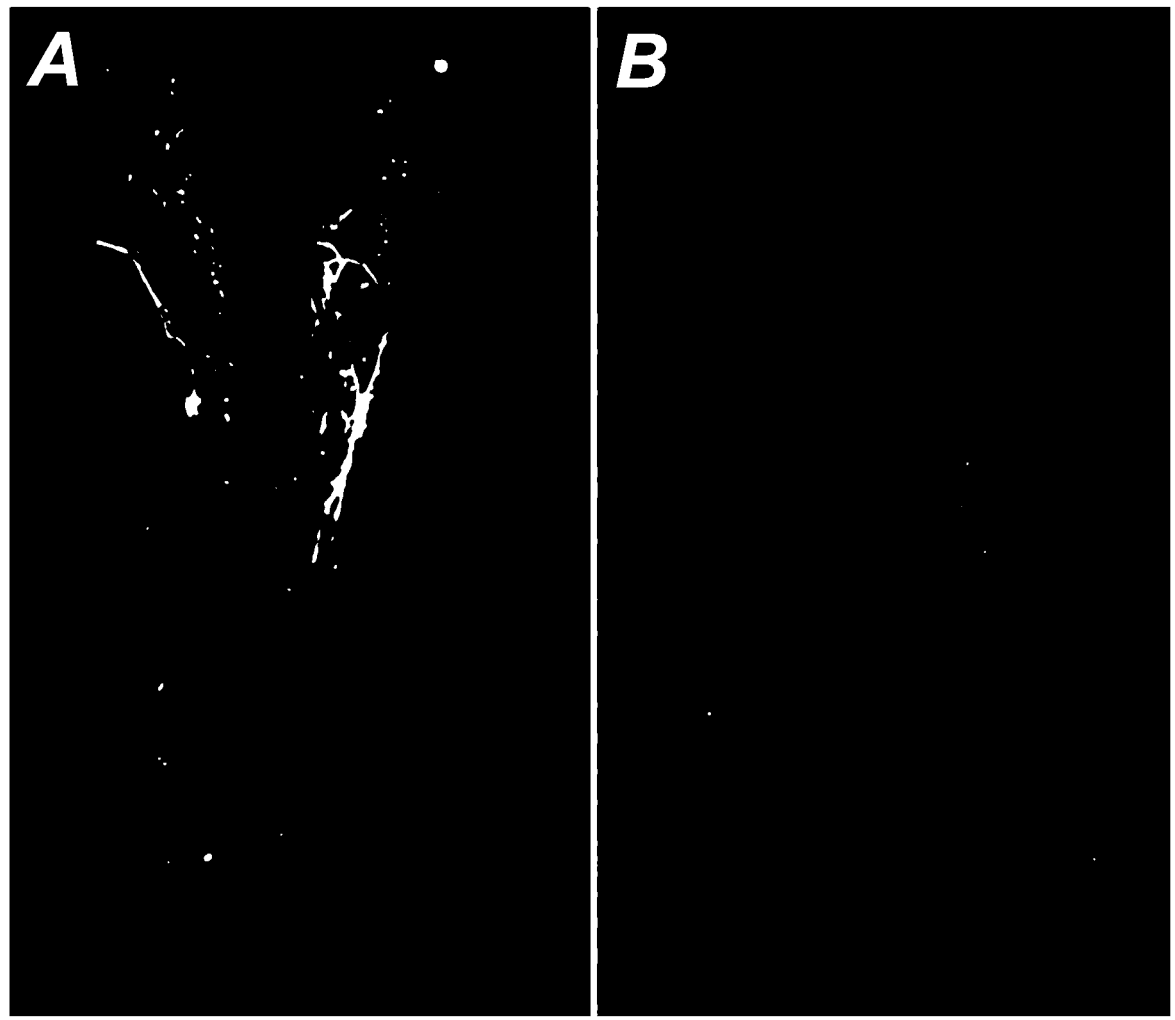
FIG. 2 shows the results of a Medtronic Maris Plus Nickel-Titanium (Nitinol) self-expanding stent that was not washed after taking it off the catheter (Panel A) and a HPG-grafted version of the same stent (Panel B) cultured in platelet rich plasma ("PRP").

FIG. 2 shows a Medtronic Maris Plus Nickel-Titanium (Nitinol) self-expanding stent that was not washed after taking it off the catheter (Panel A) and a HPG-grafted version of the same stent (Panel B).

The unmodified commercially available stent clearly exhibited significant platelet attachment and activation. This was made evident by the formation of "fibres" on the surface, which as discussed above is the result of fibrin recruitment by activated platelets through the coagulation cascade.

As can be seen, the HPG-grafted nitinol stent exhibited greatly reduced platelet attachment with no signs of platelet activation.

Figure 3:
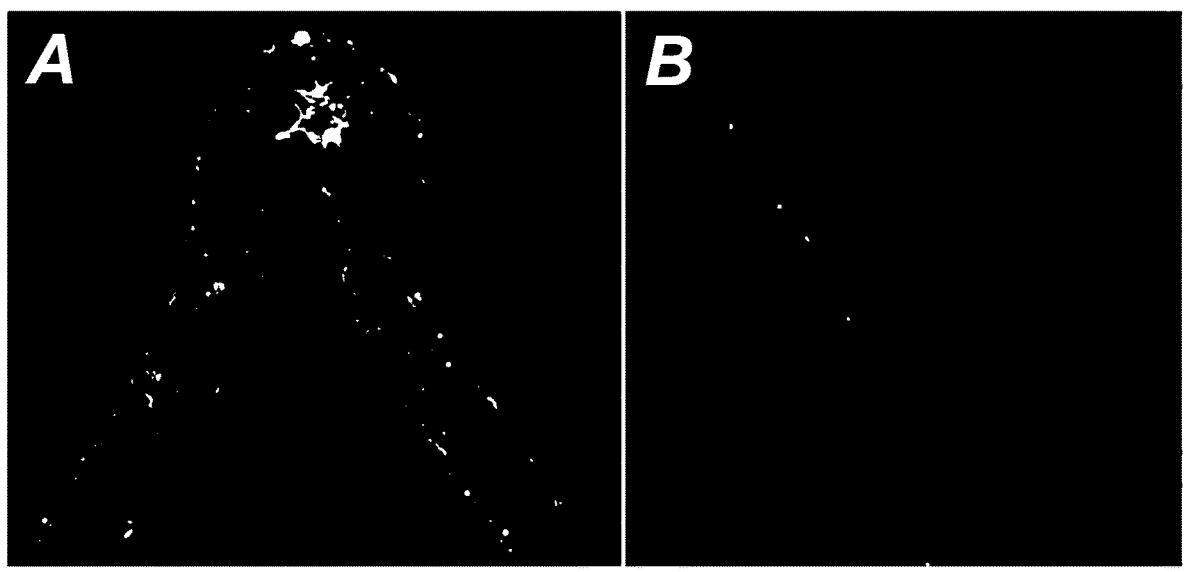
FIG. 3 shows a Medtronic Complete SE Nickel-Titanium (Nitinol) electropolished and self-expanding stent that was transferred directly from the catheter into PRP (Panel A) and a HPG-grafted version of the same stent (Panel B).

FIG. 3 shows a Medtronic Complete SE Nickel-Titanium (Nitinol) electropolished and self-expanding stent that was transferred directly from the catheter into PRP (Panel A) and a HPG-grafted version of the same stent (Panel B).

The unmodified commercially available stent clearly exhibited platelet attachment and activation. Similar to the Maris Plus stent, this was evident by the spreading of the platelets and formation of "fibres" on the surface, which is the result of fibrin recruitment by activated platelets through the coagulation cascade.

The HPG-grafted stent exhibited greatly reduced platelet attachment with no signs of platelet activation.

The effect of HPG on a cobalt chromium expanded stent was next investigated.

Figure 4:
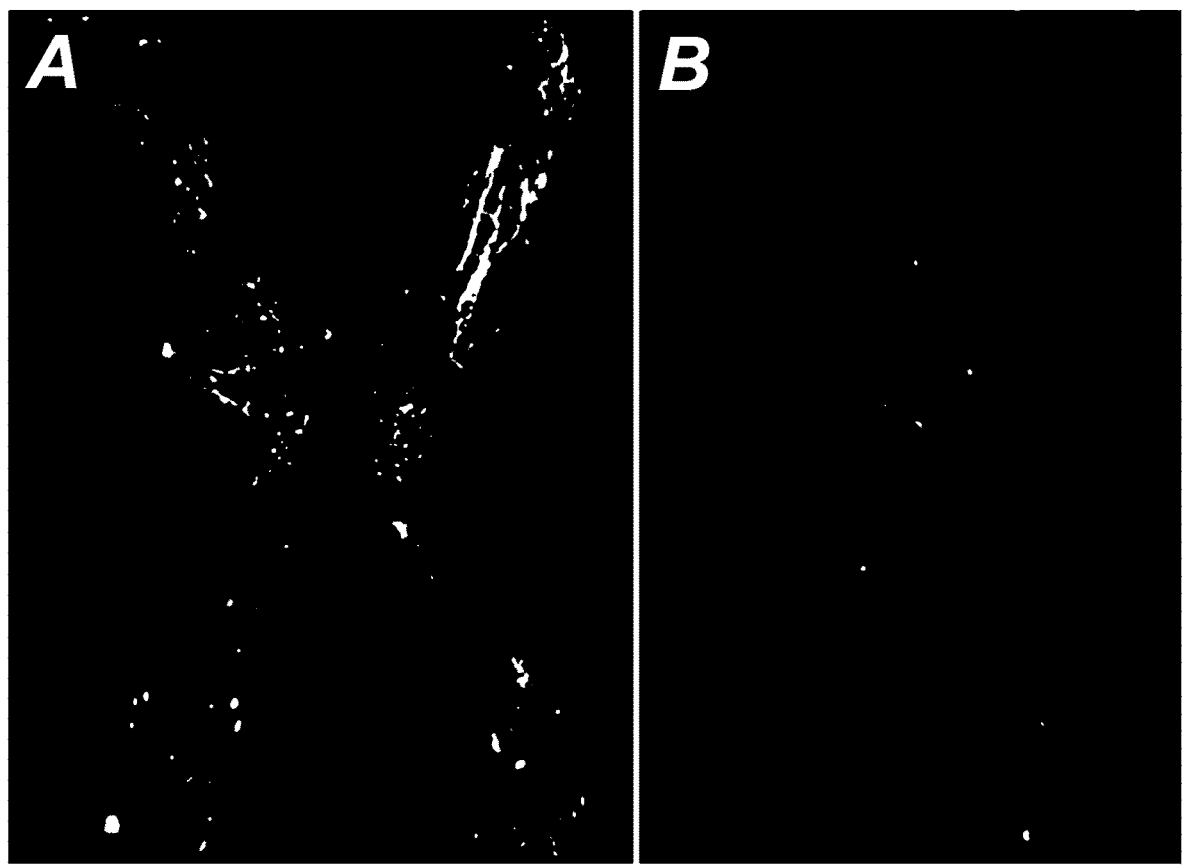
FIG. 4 shows a Medtronic Assurant Cobalt balloon expanded cobalt-chromium alloy stent that was transferred directly from the catheter, following manual expansion on the balloon catheter, into PRP (Panel A) and a HPG-grafted version of the same stent (Panel B).

FIG. 4 shows a Medtronic Assurant Cobalt balloon expanded cobalt-chromium alloy stent that was transferred directly from the catheter, following manual expansion on the balloon catheter, into PRP (Panel A) and a HPG-grafted version of the same stent (Panel B).

The unmodified commercially available cobalt-chromium alloy stent clearly exhibited platelet attachment and activation. Similar to the Maris Plus and Complete SE nitinol stents, this was made evident by the spreading of the platelets and formation of "fibres" on the surface, which is the result of fibrin recruitment by activated platelets through the coagulation cascade.

The HPG-grafted cobalt-chromium stent exhibited greatly reduced platelet attachment with no signs of platelet activation.

These results demonstrate that HPG coating of a variety of different metal alloy substrates provides a marked reduction in platelet attachment and activation associated with the substrates.

Example 3—Grafting of Hyperbranched Polyglycerol onto a Stainless Steel Substrate Results in Reduced Blood Cell Attachment Under Static and Flow Conditions We next investigated the effect of grafting HPG onto a stainless steel substrate on blood cell attachment under static conditions or flow conditions.

Figure 5:
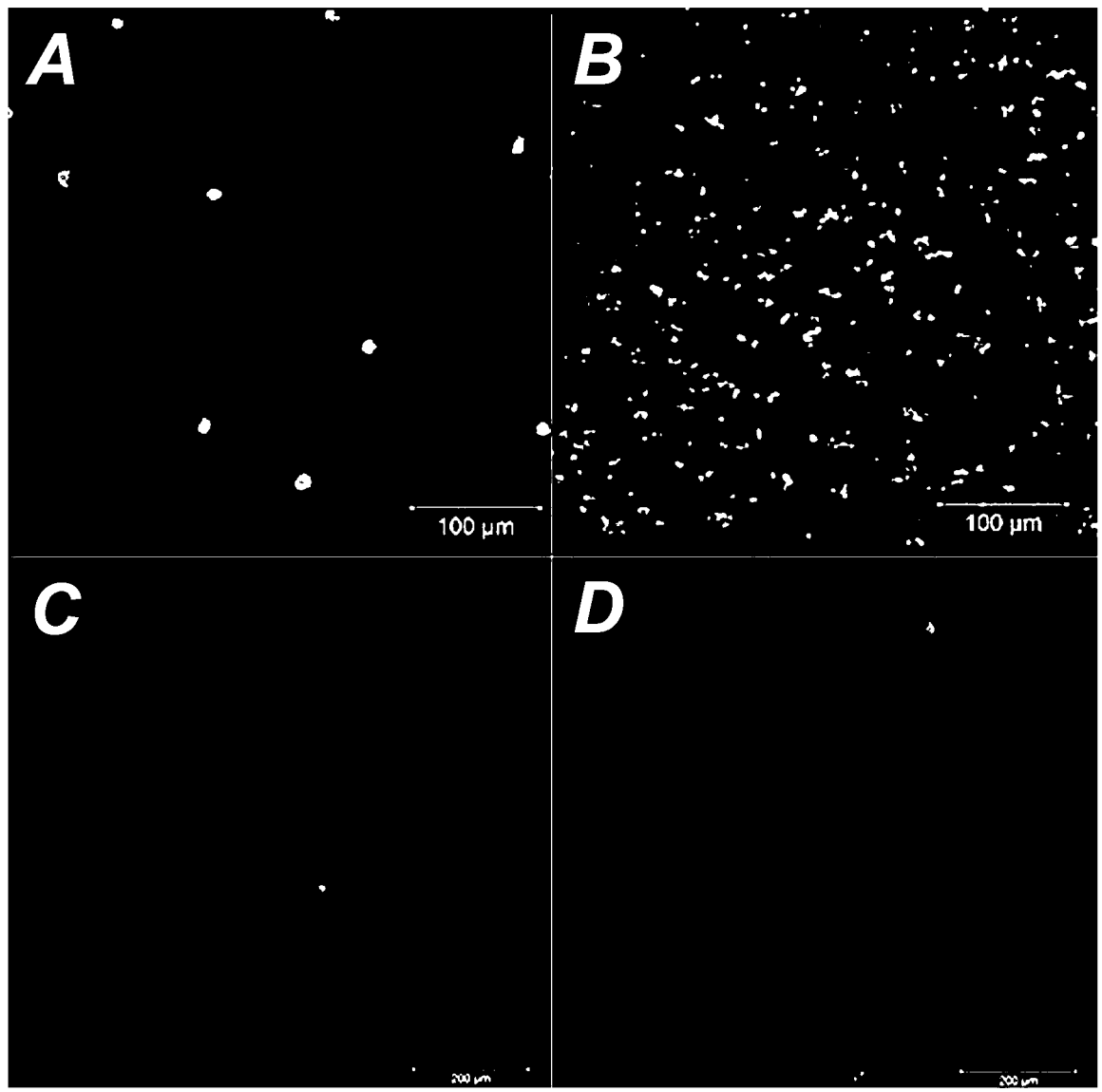
FIG. 5 shows the results of a bare stainless steel (SS) plate incubated with heparinised whole blood under static conditions (Panel A) and flowed at 2 dyne/cm2 (Panel B) for 10 minutes, compared to HPG-grafted SS plate incubated with heparinised whole blood under static conditions (Panel C) and flowed at 2 dyne/cm2 (Panel D) for 10 minutes.

FIG. 5 shows the results of a bare stainless steel (SS) plate incubated with heparinised whole blood under static conditions (Panel A) and flowed at 2 dyne/cm$^2$ (Panel B) for 10 minutes, compared to HPG-grafted SS plate incubated with heparinised whole blood under static conditions (Panel C) and flowed at 2 dyne/cm$^2$ (Panel D) for 10 minutes.

Attachment of blood cells appeared to be greatly increased on the bare SS when blood was flowed across the surface.

Conversely, the HPG-grafted substrates exhibited greatly reduced blood cell attachment under both static and flow conditions.

Discussion

The process of applying HPG to the surface of metal alloy surfaces of medical devices provided significant improvements to the biocompatibility of the material when exposed to blood products. The HPG coated substrates demonstrated greatly reduced fouling, and greatly reduced platelet attachment and activation.

By preventing the attachment and activation of platelets the risk of thrombus formation is greatly reduced. Coatings that provide such a property with reduced side effects and that display long-term stability have long been sought after yet never realised. The technology described herein is applicable to a wide variety of medical devices which have exposed metal/metal alloy surfaces, such as stents, cannulas, catheters, guide wires and valves.

The use of HPG to increase the biocompatibility of clinically relevant metals/metal alloys also provides a number of other benefits.

Firstly, the ease of application and broad compatibility of the technique is highly advantageous from a commercial point of view where the grafting process would be incorporated into existing manufacturing processes. The removal of organic solvents from the activation and grafting steps is also highly advantageous.

In addition, the oxidative and thermal stability of HPG has the potential to provide the extra stability required for long-term performance in vivo.

Example 4—Chandler Loop Experiment Comparing Off the Catheter Electropolished Nitinol Stents with HPG-Grafted Versions of the Same Nitinol Stent Using Argon A Medtronic Complete SE Iliac self-expanding stent with 6 mm diameter was removed from the catheter and cut into 4 strut sections. The sections were sonicated in DCM for 10 minutes and then fresh DCM for a further 5 minutes. Dried sections were treated with argon plasma for 20 mins at ≤2.0×10$^{-2}$ mbar. The vacuum chamber was then backfilled with argon and the stent sections placed directly into distilled glycidol and incubated for 3 h at 100° C. Excess glycidol was removed and the samples washed three times with 100% ethanol. The stent sections were then stored in 100% ethanol for 4 weeks.

Two HPG-grafted stent sections were washed 3×5 mins in MilliQ water and then inserted at either end of a 76 cm length of Tygon ND-100-65 tubing with 6.35 mm inner diameter. Stents were pushed 15 mm from each end of the tube. Control stent sections cut from a second Medtronic Complete SE Iliac self-expanding stent with 7 mm diameter were washed 3×5 mins in MilliQ water and then inserted into a second length of tube.

60 mL of whole blood was collected into a syringe primed with 28.3 µL of heparin in PBS (5 mg/mL, 0.5 units/mL). The quantity of heparin used here was designed to slow down but not completely prevent blood coagulation over the course of the experiment, so as to be able to compare the stents ability to resist or prevent thrombosis.

20 mL of the heparinized blood was quickly injected into the tubes containing the stents along with a third tube containing no stents. The tubes were formed into loops using Luer connectors made from polypropylene (Harvard Apparatus) and rotated at 4 rpm (~80 mL/min flow rate) for 2 hours at 37° C.

The tubes were opened and the blood drained. The sections of tube containing stents were cut away with a scalpel and imaged. Thrombi were removed from inside both of the control off the catheter stents and from inside the connector of the same tube.

No thrombus formed in the HPG-grafted stents or anywhere in the loop containing those stents. Thrombus formed in the connector of the control loop containing no stents, which may have been due to a lower volume of blood as compared to the other two containing stents and therefore a higher air to blood ratio. Thrombi from the two tubes were imaged. Following thrombus removal, the tube around the stents was cut lengthwise and the stents removed, washed lightly in PBS and fixed in 4% paraformaldehyde in PBS.

Figure 6:
FIG. 6 shows an ex vivo chandler loop assay comparing the anti-thrombotic potential of a) HPG-grafted nitinol stents with b) bare nitinol stents after flowing heparinised blood for 2 hours at 37° C. The resulting blood clots retrieved from the bare nitinol stents can be seen in c), while no substantial clots formed in the HPG-grafted stents.

The results are shown in FIG. 6. Panel a) depicts the lumen on the HPG-grafted nitinol stents following the Chandler loop assay. No measurable quantity of thrombus could be removed from the lumen. Panel b) depicts the bare nitinol stent controls following the same Chandler loop assay, and shows that the lumen of one stent was completely blocked by thrombus while the other stent contained a lower yet measurable quantity of thrombus. Panel c) depicts the thrombus removed from the control stents in panel b).

This data demonstrates the improved patency of HPG-grafted nitinol stents when compared to unmodified nitinol stents under induced thrombosis formation conditions. This data support the fact that coating of the stents leads to a reduction in thrombosis associated with the stents, and a reduced formation of occlusive thrombi in the stents.

Example 5—Chandler Loop, and Neutrophil and Complement Activation for Coated Stents Stent Preparation and Chandler Loop Assay HPG-grafted stents were modified first by activation in argon plasma for 20 minutes and then incubation in neat distilled glycidol for 24 hours at 100° C., washed in methanol three times and stored in methanol until use. HPG-grafted stents were stored up to 1 month in methanol before use.

HPG-grafted Cook Medical Zilver stent sections and control Cook medical Zilver (nitinol) stent sections were washed in sterile water three times over a period of one hour. Stent sections were then washed in sterile PBS (phosphate buffered saline, pH 7.4) three times over a period of 30 minutes.

Tygon ND-100-65 tubing with internal diameter of 6.35 mm was cut into two lengths under sterile conditions such that the volume of each tube was 10 mL. HPG-grafted and control Zilver stent sections were loaded into separate tubes and labelled appropriately. Each tube was formed into a loop and closed shut using an external sleeve at the joint so as to maintain the internal diameter throughout the entire loop. This was important for preventing turbulence as the blood moved through the tube. 20 mL of whole blood was taken from healthy male and female donors of various ages. Blood was drawn directly into a 20 mL syringe pre-loaded with 0.5 U/mL of heparin in 1 mL of sterile PBS. Blood in the syringe was gently mixed by repeated inversion to ensure complete dispersion of heparin. Within 2 minutes of the blood being taken, 10 mL was injected into each loop containing the stent sections through a 19 gauge needle with a 26 gauge needle used as a vent to let the air escape. The tubes filled with blood were then rotated at a shear rate of either 70/s or 125/s for between 1 hour and 3 hours at 37° C. The tubes were then cut open and the contents poured into petri dishes for assessment. Stents and clots were removed from liquid blood, weighed, rinsed in PBS and photographed.

Complement and Neutrophil Assays

For complement and neutrophil assays, the following modifications were applied to the Chandler loop assay: Whole blood was drawn into 9 mL Vacuette Tubes containing Lithium Heparin. One of these tubes was kept as a native blood control and was maintained at room temperature with slow rocking. The remaining tubes were combined and syringed into the loops containing the stents sections. One loop containing no stent was also filled with blood to measure any effect the tubing itself had on the blood. The loops were rotated at 37° C. for 1 hour then the liquid blood removed from each loop and tested within 1 hour of being removed from the Chandler loop.

Figure 7:
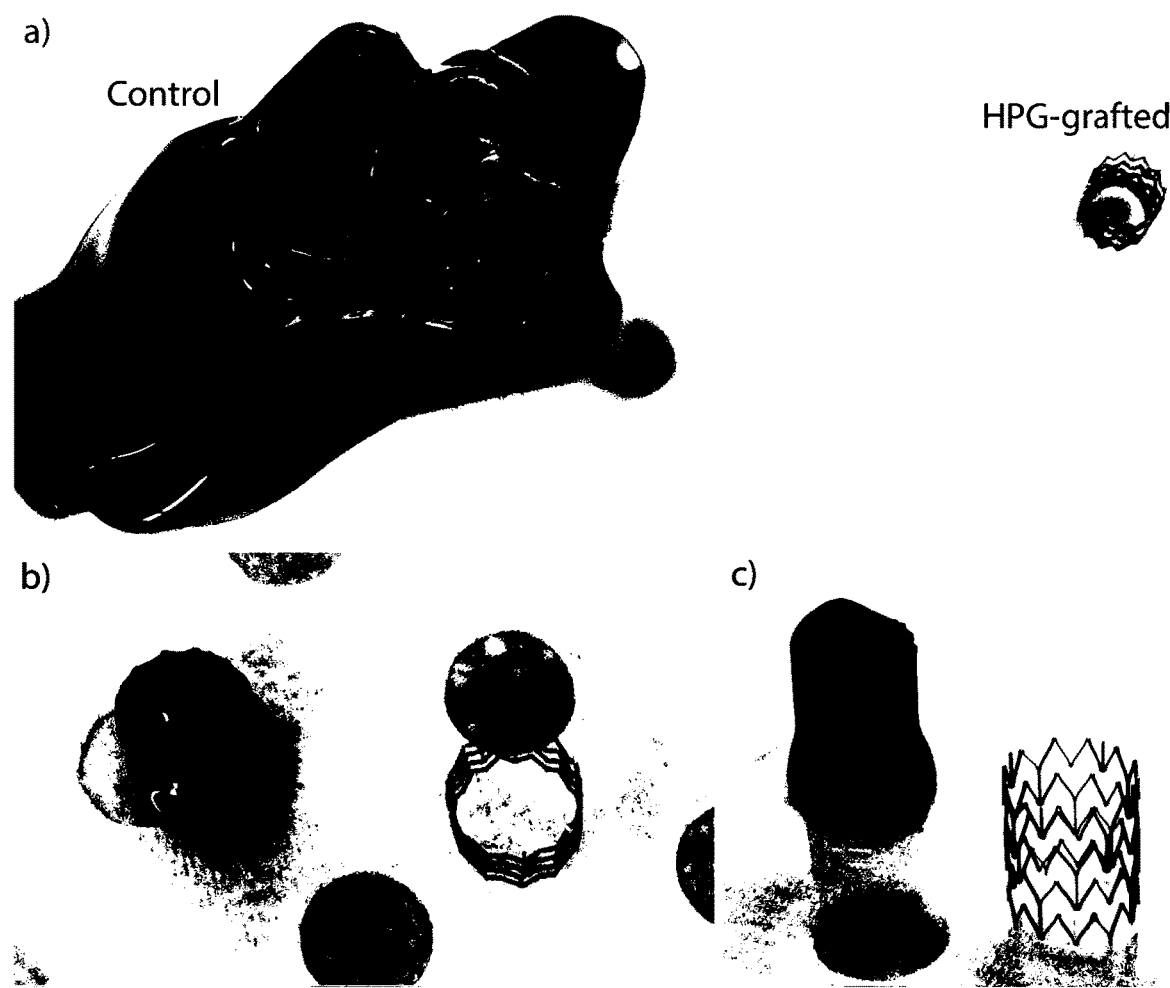
FIG. 7 shows representative photographs of 7 mm long sections of Cook Medical Zilver stents and HPG-grafted Zilver stents following 2.5 hours in heparinised human whole blood (0.5 U/mL heparin) under flow at 37° C. Photograph a) was captured immediately following removal of stent sections from the ex vivo chandler loop assay with control stent on the left and the HPG-grafted stent on the right. Photographs b) and c) were captured after the control stent was cut away from the blood clot that extended outside the stent and both control and HPG-grafted stents were rinsed lightly in PBS (phosphate buffered saline, pH 7.4) to remove liquid blood.

The data is shown in FIG. 7, which shows representative photographs of 7 mm long sections of the Cook Medical Zilver nitinol stents and HPG-grafted Zilver stents following 2.5 hours in heparinised human whole blood (0.5 U/mL heparin) under flow at 37° C.

Control stents consistently formed large clots that would completely occlude the stent and often protrude outside the stent. HPG-grafted stents consistently exhibited little to no clot formation under the same conditions as the controls. The results demonstrated in FIG. 7 indicate that HPG-grafted nitinol stents have much lower thrombotic potential when compared to the bare nitinol Zilver stents.

Photograph a) was captured immediately following removal of stent sections from the ex vivo chandler loop assay with control stent on the left and the HPG-grafted stent on the right. Photographs b) and c) were captured after the control stent was cut away from the blood clot that extended outside the stent and both control and HPG-grafted stents were rinsed lightly in PBS (phosphate buffered saline, pH 7.4) to remove liquid blood.

Figure 8:
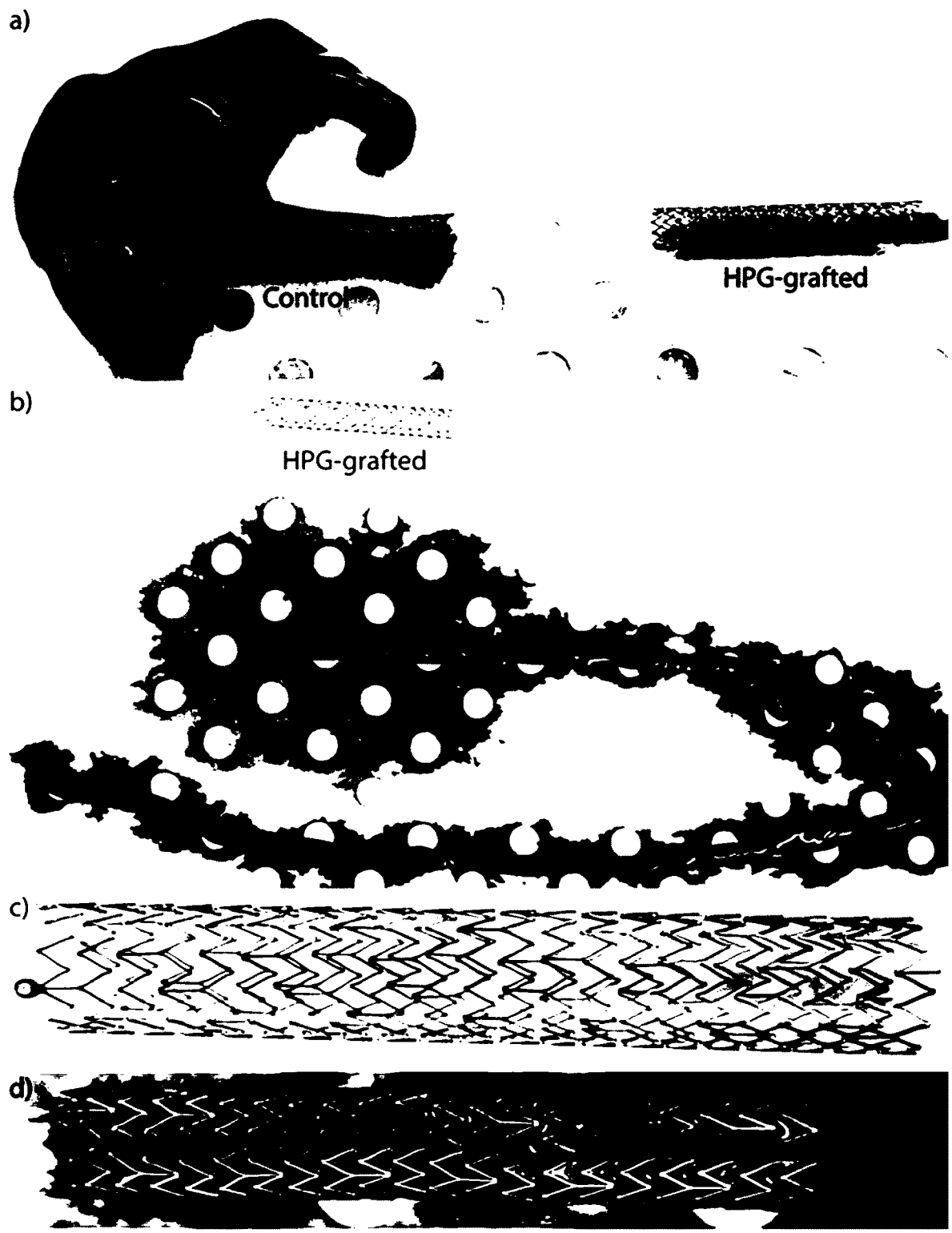
FIG. 8 shows representative photographs of 40 mm long sections Cook Medical Zilver stents and HPG-grafted Zilver stents following 1 hour in heparinised human whole blood (0.5 U/mL heparin) under flow at 37° C. Photograph a) was captured immediately following removal of stent sections from the ex vivo chandler loop assay with control stent on the left and the HPG-grafted stent on the right. Photographs b), c) and d) were captured after both control and HPG-grafted stents were rinsed lightly in PBS (phosphate buffered saline, pH 7.4) to remove liquid blood.

FIG. 8 shows representative photographs of 40 mm long sections Cook Medical Zilver stents and HPG-grafted Zilver stents following 1 hour in heparinised human whole blood (0.5 U/mL heparin) under flow at 37° C. Photograph a) was captured immediately following removal of stent sections from the ex vivo chandler loop assay with control stent on the left and the HPG-grafted stent on the right. Photographs b), c) and d) were captured after both control and HPG-grafted stents were rinsed lightly in PBS (phosphate buffered saline, pH 7.4) to remove liquid blood.

Control stents of clinically relevant length consistently formed large clots that would completely occlude the stent and often protrude outside the stent. HPG-grafted stents of clinically relevant length consistently exhibited little to no clot formation under the same conditions as the controls. The results demonstrated in FIG. 8 indicate that HPG-grafted nitinol stents have much lower thrombotic potential when compared to the bare nitinol Zilver stents.

Table 1 summarizes the results from DHR and CH50 assays along with platelet counts on Cook Medical Zilver nitinol stents.

Donor blood was collected into 9 mL Vacuette Tubes containing Lithium Heparin. One tube (native blood) was left at room temperature with slow rocking motion, the remaining tubes were combined then used to fill three loops of plastic tubing. One loop (control blood) contained just blood with no stent, the two other loops contained either a bare control stent or a HPG-coated stent. The loops where rotated at 37° C. for 1 hour then the liquid blood removed from each loop and tested.

The dihydrorhodamine (DHR)-123 oxidative burst assay is a flow cytometric test to measure the oxidative burst in neutrophils. The DHR assay for neutrophil activation is measured in mean fluorescence intensity (MFI) and uses an artificially activated control using phorbol myristate acetate (PMA), which represents level of activation from an extreme inflammatory event. This assay was commissioned through SA Pathology and run per their accredited diagnostic procedure. Results indicate there was no significant neutrophil activation for either bare nitinol Zilver stents or HPG-grafted Zilver stents.

The CH50 assay can be considered as a screening assay for complement activation, it is sensitive to the reduction, absence and/or inactivity of the components of the classical pathway and membrane attack pathways. The CH50 assay measures complement activation through reduction in complement components. This assay was commissioned through SA Pathology and run as per their accredited diagnostic procedure. Results indicate there was no complement activation observed for either bare nitinol Zilver stents or HPG-grafted Zilver stents.

DHR—Test for neutrophil activation measured in mean fluorescence intensity (MFI); Ctl=DHR+PMA which represents level of activation from an extreme inflammatory event.

CH50—Measure of complement activation through reduction in complement components; there was no neutrophil or complement activation observed for either uncoated or HPG-coated Zilver stents.

Table 1 summarizes the results from DHR and CH50 assays along with platelet counts from blood flow over Cook Medical Zilver nitinol stents.

Results from these assays indicate there is no difference in neutrophil or complement activation between the clinical grade bare nitinol Zilver stents and the HPG-grafted Zilver stents. Therefore, it can be concluded that the addition of the HPG coating does not trigger neutrophil or complement activation when applied to nitinol stents. The platelet counts also indicate that the HPG coating does not result in greatly reduced platelet numbers in the blood, and therefore platelets are not attaching to the stent surface.

TABLE 1

| Donor | | Unit | Native Blood | Control Blood | Uncoated stent | HPG-coated stent |
|---|---|---|---|---|---|---|
| #1 M | DHR (ctl = 32989) | MFI | 329 | 327 | 293 | 452 |
| | CH50 | % | 95.2 | 98 | 101 | 99.4 |
| | PLT | 10^9/L | 156 | 137 | 157 | 143 |
| #7 F | DHR (ctl = 6453) | MFI | 164 | 182 | 150 | 178 |
| | CH50 | % | 70.6 | 75 | 74 | 76.4 |
| | PLT | 10^9/L | 166 | 154 | 152 | 134 |
| #3 M | DHR (ctl = 14145) | MFI | 219 | 192 | 194 | 249 |
| | CH50 | % | 92.0 | 86.8 | 85.7 | 86.9 |
| | PLT | 10^9/L | 123 | 119 | 95 | 116 |
| #4 F | DHR (ctl = 23725) | MFI | 138 | 131 | 134 | 145 |
| | CH50 | % | 99.2 | 99.8 | 101.3 | 101.9 |
| | PLT | 10^9/L | 74 | 83 | 90 | 90 |
| #5 F | DHR (ctl = 30475) | MFI | 311 | 295 | 302 | 308 |
| | CH50 | % | 145.6 | 141.7 | 134.3 | 134.5 |
| | PLT | 10^9/L | 104 | 122 | 103 | 116 |

Example 6—Manufacture of HPG Coated Stents

For the production of a HPG alloy stent, initially rounded wire of the selected metal/metal alloy (for example made from nitinol, or cobalt chromium alloy) may be provided. The wire may be formed into sinusoids before being wrapped onto a mandrel with crown to crown alignment, to square up the ends of the stent. Fusion points in the stent may then be laser fused. The stent may then be electropolished to provide a polished surface area of the round struts and wrap-crimped for a low profile.

The stent may then be subject to sonication in dichloromethane for 10 minutes and a subsequent round of further sonication in 5 minutes in fresh dichloromethane undertaken.

The clean stent may then be dried under a stream of nitrogen gas and placed at the centre of the vacuum chamber of a plasma cleaner fitted with an oxygen gas line-in. The vacuum chamber is pumped down to a pressure $<2.0 \times 10^{-2}$ mbar with intermittent purging with pure argon to ensure minimal atmospheric contamination in the chamber. Upon reaching the desired pressure, radio frequency (RF) induced plasma may be used at maximum power (18 W RF output) for 20 minutes.

Following plasma treatment the chamber may then be backfilled with pure argon and the stent transferred directly into distilled glycidol and then incubated at 100° C. for up to 24 hours to coat the stent with HPG.

Following incubation, the stent may be washed ×3 with 100% ethanol and then soaked in 100% ethanol for at least 24 hours, prior to use or storage.

Example 7—Use of a HPG Coated Stent for Coronary Angioplasty

A metal alloy stent may be coated with HPG as described in Examples 1 or 4, or a HPG coated stent may be manufactured as described in Example 6.

Procedures for the use of a stent in an angioplastic procedure are known in the art. An example of a procedure for use of a HPG coated stent is described below.

Prior to the procedure, the medical practitioner may place a patient on aspirin and/or other medication for several days prior to the procedure to assist with reducing blood clots forming during the stent procedure.

To perform coronary angioplasty, the coated stent may be inserted into a coronary artery through a catheter. The stent procedure will typically begin with an angiography test to determine the number and exact location of any blockages. After the medical practitioner has determined which blockages need treatment, the medical practitioner will implant the coated stent:

With x-ray guidance, the medical practitioner will advance a thin wire through the catheter to the treatment site in the coronary artery to penetrate the blockage and provide support for the stent delivery system.

A tiny deflated balloon will be advanced to the blockage along the wire that is already in place. Once the balloon is inside the blockage, the balloon will be inflated to squeeze the plaque against the wall of the coronary artery and to widen the arterial opening.

Next, another deflated balloon with the coated stent mounted on it will be advanced to the blockage. Once the coated stent is inside the blockage, the balloon is inflated, thereby expanding the stent that surrounds it. The coated stent locks in place against the artery wall, forming a scaffold to help keep the artery open.

After the stent has been fully expanded, additional X-ray imaging is taken to determine if the stent is fully open and how much blood flow has been improved. The medical practitioner may inflate the balloon additional times to be certain the stent is firmly pressed against the vessel wall.

Once the medical practitioner is satisfied that the coated stent is fully open and adequate blood flow has been restored, the balloon catheter, guidewire, and guide catheter are removed.

It is anticipated that the HPG coated stent will provide an improvement to thrombosis associated with the introduction of the stent.

The use of a HPG coated stent may also result in a reduction in the dose, timing and/or duration of anti-clotting agent(s) required to be administered to a patient after the procedure as compared to bare metal/metal alloy stents. A coated stent may also provide improvements in the efficacy of stent action and/or longevity.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of reducing fouling and/or thrombosis associated with a medical device comprising a metallic substrate, the method comprising activating the metallic substrate by plasma treatment and coating the metallic substrate with a hyperbranched polyglycerol by exposing the activated metallic substrate to pure glycidol or a solution comprising at least 90% glycidol.

2. The method according to claim 1, wherein the coating of the metallic substrate comprises polymerisation of glycidol monomers on the metallic substrate.

3. The method according to claim 1, wherein the coating comprises activation of the metallic substrate by plasma treatment in the presence of an inert and/or non-depositing gas.

4. The method according to claim 1, wherein the medical device comprises a stent, a cannula, or a valve.

5. The method according to claim 4, wherein the stent, the cannula or the valve comprises a metallic substrate comprising a steel alloy, a nickel titanium alloy or a cobalt chromium alloy.

6. A method of coating a metallic substrate with a hyperbranched polyglycerol, the method comprising polymerisation of glycidol monomers to form a hyperbranched polyglycerol on the metallic substrate activated by plasma treatment and exposing the plasma activated metallic substrate to pure glycidol or a solution comprising at least 90% glycidol and thereby coating the substrate with the hyperbranched polyglycerol.

* * * * *